United States Patent
Eisenkolb

(10) Patent No.: US 8,230,769 B2
(45) Date of Patent: Jul. 31, 2012

(54) DEVICE FOR PREPARING TISSUE DISCS, IN PARTICULAR CARTILAGINOUS DISCS

(75) Inventor: Peter Eisenkolb, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 297 days.

(21) Appl. No.: 12/134,776

(22) Filed: Jun. 6, 2008

(65) Prior Publication Data
US 2008/0306500 A1 Dec. 11, 2008

(30) Foreign Application Priority Data
Jun. 8, 2007 (DE) .......... 10 2007 026 574

(51) Int. Cl.
B26D 5/08 (2006.01)
A61B 17/32 (2006.01)
(52) U.S. Cl. .......... 83/607; 83/609; 83/614; 83/694; 606/167; 606/151; 606/207
(58) Field of Classification Search ............. 83/604, 83/614, 387, 375, 453, 597, 509, 594, 694, 83/542, 609; 606/167, 151, 207, 182, 157, 606/158, 159, 176; 264/406; 30/134, 253, 30/258; 623/23.51, 23.72; D24/147, 146, D24/135, 137, 138, 140
See application file for complete search history.

(56) References Cited

U.S. PATENT DOCUMENTS

| | | | |
|---|---|---|---|
| 1,918,700 A | 7/1933 | Harris | |
| 2,660,221 A * | 11/1953 | Simpson | 156/506 |
| 3,175,556 A | 3/1965 | Wood et al. | |
| 4,092,774 A * | 6/1978 | Watts | 30/92 |
| 4,228,707 A | 10/1980 | Arlett | |
| 4,243,047 A * | 1/1981 | Olsen | 600/564 |
| 4,394,796 A * | 7/1983 | Winer | 30/178 |
| 4,764,243 A * | 8/1988 | Shioiri et al. | 156/505 |
| 4,938,215 A * | 7/1990 | Schulman et al. | 606/120 |
| 6,228,097 B1 * | 5/2001 | Levinson et al. | 606/142 |
| 6,477,776 B1 * | 11/2002 | Jee | 30/90.1 |
| 6,852,117 B2 * | 2/2005 | Orlowski | 606/120 |
| 7,559,940 B2 * | 7/2009 | McGuire et al. | 606/184 |
| 2003/0125811 A1 | 7/2003 | Bonutti | |

FOREIGN PATENT DOCUMENTS

| EP | 0134750 B1 | 3/1985 |
|---|---|---|
| WO | 83/00994 A1 | 3/1983 |
| WO | 2008008240 A2 | 1/2008 |

OTHER PUBLICATIONS

German Search Report, Feb. 29, 2008, 4 pages.
European Search Report, EP08008084, Sep. 24, 2008, 6 pages.

* cited by examiner

Primary Examiner — Ghassem Alie
(74) Attorney, Agent, or Firm — St. Onge Steward Johnston & Reens LLC

(57) ABSTRACT

The invention relates to a device for preparing tissue discs, in particular cartilaginous discs. A device for preparing tissue discs that is of simple structure and ensures safe handling includes, in addition to a clamping device for securing a tissue block by clamping, at least one cutting device for treating the tissue block held in the clamping device.

8 Claims, 3 Drawing Sheets

DEVICE FOR PREPARING TISSUE DISCS, IN PARTICULAR CARTILAGINOUS DISCS

CROSS-REFERENCE TO RELATED APPLICATIONS

The present application claims priority of German patent application No. 10 2007 026 574.5 filed on Jun. 8, 2007 the content of which is incorporated herein by reference.

FIELD OF THE INVENTION

The invention relates to a device for preparing tissue discs, in particular cartilaginous discs.

BACKGROUND OF THE INVENTION

In preparing tissue discs, for instance to create a new nasal septum from a transplanted rib, it is essential that the plastic material that is to be created be prepared to a predetermined strength. In practice this preparation is performed manually by means of a scalpel. Aside from the fact that this skilled preparation by a scalpel poses a high risk of injury for the user, it is extremely difficult to ensure precise dimensions for the plastic material, in particular concerning the thickness of the tissue disc.

It is therefore the object of the invention to create a device for preparing tissue discs that guarantees both simplicity in structure and safe and precise operation.

SUMMARY OF THE INVENTION

This object is fulfilled according to the invention by a device for preparing tissue discs, in particular cartilaginous discs, said device including a clamping device for securing a block of tissue by clamping and having at least one cutting device for treating the tissue block held in the clamping device.

Because of the inventive combination of a clamping device and a cutting device in one apparatus, it is possible for the first time to prepare tissue discs of predetermined size and thickness quickly and precisely. With the inventive device, one can do away completely with the use of a scalpel as is common in the art.

According to a practical embodiment of the invention, it is proposed that the clamping device should comprise at least two clamping jaws, where at least one clamping jaw can be displaced with respect to the at least one other clamping jaw.

To avoid squeezing too strongly the tissue block that is to be secured by the clamping device on the one hand, while on the other hand still securing the tissue block, it is proposed with the invention that, when the clamping device is in closed position, there should remain, between the at least two clamping jaws of the clamping device, a clamping gap whose height is advantageously adjustable, so that the device can be used for various tissue disc sizes.

It is proposed, with a preferred embodiment of the invention, that the clamping device should comprise one rigid clamping jaw that is mounted on a base body, and one clamping jaw that can rotate with respect to the rigid clamping jaw.

According to the invention, the rigid clamping jaw is advantageously configured as a double-walled plate with a window-like opening in such a way that the clamping jaw that can rotate with respect to the rigid clamping jaw is mounted so that it can move within an intermediate space between the two side walls of the double-walled plate which are distanced from one another. This arrangement of the rotatable clamping jaw within the intermediate space of the rigid clamping jaw ensures a precise motion of the rotatable clamping jaw, free of canting.

The thickness of the tissue disc that is to be prepared can vary according to the invention owing to the fact that the breadth of the intermediate space formed by the side walls of the double-walled plate is adjustable.

For mounting the rotatable clamping jaw, it is proposed that it should be mounted on one side in the plate of the rigid clamping jaw, so that the height of the clamping gap remaining free between the rigid and the rotatable clamping jaw can be adjusted in the plate by displacing the mounting point of the rotatable clamping jaw.

To be able to hold the tissue block that is to be prepared securely and immovably in the clamping gap, it is proposed according to the invention that tooth-like fixing elements should be configured at least on the mutually facing surfaces of the at least two clamping jaws.

For configuring the cutting device, according to a practical embodiment of the invention it is proposed that the cutting device should be configured as a swivel arm that can be displaced with respect to the clamping device and that is equipped with at least one cutting edge, and that said swivel arm advantageously should be mounted so that it can rotate either on the base body or on the plate of the rigid clamping jaw.

According to a preferred embodiment of the invention, it is further proposed that the swivel arm, at least in the area of the at least one cutting edge, should comprise two arm parts running parallel to one another and each equipped with a cutting edge, said arm parts are mounted on the base body or on the plate of the rigid clamping jaw in such a way that the plate is positioned between the two arm parts. This inventive configuration of the cutting device makes possible the simultaneous treatment of two parallel pieces for preparing the tissue disc.

To be able to guarantee a constantly uniform cutting quality, it is further proposed that the at least one cutting edge should be positioned replaceably on the swivel arm. The replaceability of the cutting edge has the advantage, moreover, that only the cutting edge that is immediately below the direct abrasion needs to be replaced, rather than the entire swivel arm.

It is finally proposed with the invention that the distance of the two parallel arm parts and thus also of the two cutting edges to one another should be adjustable. Thanks to this variation in the cutting edge distance to one another, the thickness of the tissue disc that is to be prepared can be easily and reliably adjusted and maintained.

The invention also relates to a cutting device for a device for preparing tissue discs, in particular cartilaginous discs, having a clamping device for securing a tissue block by clamping. To ensure both simple structure and a safe and exact handling of the cutting device, the inventive cutting device is distinguished in that it is configured as a swivel arm that can be displaced with respect to the clamping device and is equipped with at least one cutting edge.

Additional characteristics and advantages of the invention can be seen by referring to the appended illustrations, in which an embodiment of an inventive device for preparing tissue discs, in particular cartilaginous discs, is depicted in merely exemplary terms, with restricting the invention to this embodiment.

DETAILED DESCRIPTION OF THE INVENTION

Figure 1:
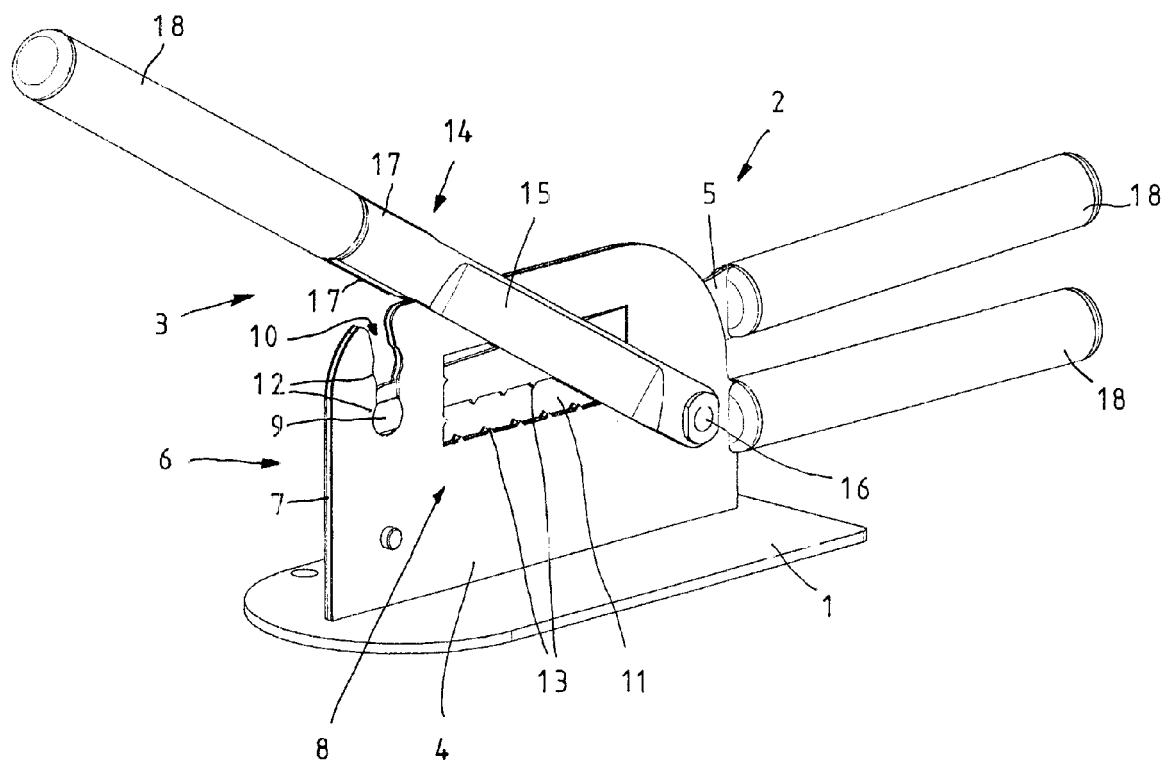
FIG. 1 shows a perspective side view of an inventive device for preparing tissue discs, depicting a first working position.
Figure 2:
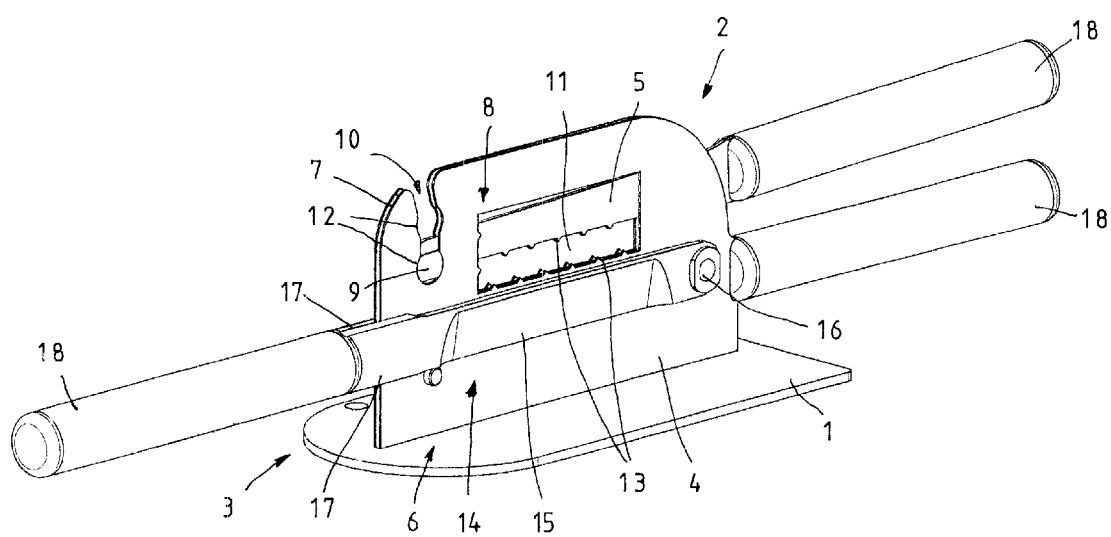
FIG. 2 shows a view according to FIG. 1 but depicting a second working position.
Figure 3:
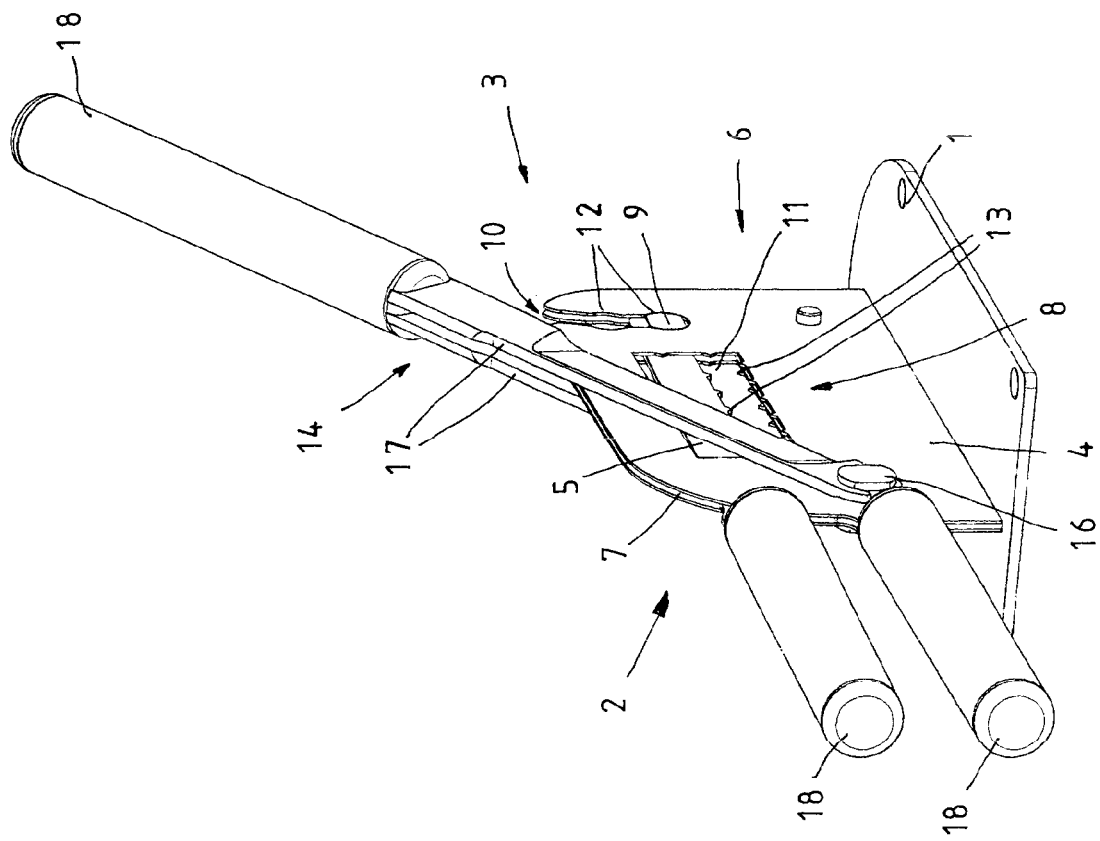
FIG. 3 shows a view as in FIG. 1 rotated by 180 degrees.

The device illustrated in FIGS. 1 through 3 for preparing tissue discs, in particular cartilaginous discs, consists essentially of a base body 1 serving as support surface and of a clamping device 2 and a cutting device 3, which are mounted on the base body 1.

This type of device serves for preparing tissue discs, for example for creating a new nasal septum from a transplanted rib piece. It is also possible of course to process other tissue, possibly including synthetic tissue, with this device.

In the illustrated embodiment the clamping device 1 consists of a rigid clamping jaw 4 and a clamping jaw 5 that can rotate with respect to the rigid clamping jaw 4. As can be seen from the illustrations, the rigid clamping jaw 4 is configured as a double-walled plate 6 in such a way that the two side walls are distanced from one another so as to form an intermediate space 7. For inserting a tissue block that is to be prepared, a window-like opening 8 is configured in the plate 6.

The clamping device 2 is completed by the rotatable clamping jaw 5, which, as can be seen from the illustrations, is mounted movably in the intermediate space 7 formed by the double-walled plate 6 of the rigid clamping jaw 4, so that the actual rotatable mounting of the rotatable clamping jaw 5 occurs by means of a positioning pin 9 that is positioned on one end of the clamping jaw 5 and that can be inserted into a positioning recess 10 configured in the plate 6 of the rigid clamping jaw 4.

As can be seen in particular from FIG. 2, the clamping device 2 is configured in such a way that, also when the clamping device 2 is in the closed position, that is, when the rotatable clamping jaw 5 has been rotated downward, partly closing the window-like opening 8, an open clamping gap 11 for clamping insertion of the tissue disc that is to be prepared remains between the rotatable clamping jaw 5 and the upper edge of the rigid clamping jaw 4.

In the illustrated embodiment the positioning pin 9 of the rotatable clamping device 5 is configured as non-round in such a way that the rotatable clamping jaw 5 can be inserted into the positioning recess 10 only in a position aligned basically perpendicular to the base body 1 and in the positioning recess 10 individual mounting points 12 are configured in which the rotatable clamping jaw 5 can be rotated downward in the direction of the window-like opening 8 of the plate 6 to close the clamping device 2. To be able to vary the height of the clamping gap 11 for inserting larger or smaller tissue blocks, several mounting points 12 are configured, positioned above or below one another for rotatable mounting of the rotatable clamping jaw 5.

In addition the clamping device 2, at least on the mutually facing surfaces of the rigid clamping jaw 4 and of the rotatable clamping jaw 5, comprises tooth-like fixing elements 13, which ensure a secure and immovable bracing of the tissue blocks positioned for processing in the clamping device 2.

The cutting device 3 in the illustrated embodiment consists of a swivel arm 14 that is configured so that it can rotate with respect to the clamping device 2 and that comprises at least one cutting edge 15 for cutting the tissue block held in the clamping device 2, where the swivel arm 14 in the illustrated embodiment is mounted rotatably on a mounting pin 16 shaped on the plate 6. Alternatively it is also possible, of course, to mount the swivel arm 14 on the base body 1.

To be able to ensure a constantly uniform cutting quality, the at least one cutting edge 15 is preferably positioned replaceably on the swivel arm 14.

In the illustrated embodiment the swivel arm 14 comprises two arm parts 17 that run parallel to one another and are each equipped with a cutting edge 15 and mounted on the plate 6 in such a way that the plate 6 is positioned between the two arm parts 17 of the swivel arm 14. This configuration of the cutting device 3 makes possible the simultaneous execution of two parallel cuts for preparing a tissue disc from the tissue block held in the clamping device 2.

To be able to produce tissue discs of varying thicknesses by means of the cutting device 3, there exist two possibilities for altering the distance between the two arm parts 17 of the swivel arm 14 of the cutting device 3, namely, first the alteration of the width of the intermediate space 7 configured between the side walls of the double-walled plate 6, by widening or narrowing the side wall distance of the plate 6, and second alteration of the distance between the two arm parts 17 of the swivel arm 14 of the cutting device 3 without changing the widths of the intermediate space 7 formed between the side walls of the double-walled plate 6.

Alternatively to the illustrated configuration of the cutting device 3 with a rotatably mounted swivel arm 14, it is also possible of course to configure the cutting device 3 in such a way that the cutting device 3 comprises at least one cutting arm that can slide axially with respect to the clamping device 2 and that is equipped with at least one cutting edge 15. The axial mobility of the cutting arm with respect to the clamping device 2 makes it possible to exert a sawing cutting motion of the cutting device 3.

The assembly and operation of the above-described device for preparing tissue discs occur as follows.

Before the use of the device, the rotatable clamping jaw 5 and the swivel arm 14 of the cutting device 3 are first connected with the device. For this purpose the rotatable clamping jaw 5 is inserted into the positioning recess configured in the double-walled plate 6, in a position aligned essentially perpendicular to the base body 1 with the positioning pin 9 in front, until the positioning pin 9 reaches mounting point 12, which corresponds to the height of the clamping gap 11 that is necessary for the particular purpose.

Then the rotatable clamping jaw 5 can be rotated 90 degrees downward until the particular minimal height of the clamping gap 11 is reached.

Next the swivel arm 14 of the cutting device is placed on the mounting pin 16 configured on the plate 6, for which purpose a mounting recess that corresponds with the contour of the mounting pin 16 is configured on the front end of the swivel arm 14. To prevent accidental separation of the swivel arm 14 from the mounting pin 16, the mounting pin 16 is of non-round configuration so that the swivel arm 14 can be mounted on the mounting pin 16 only in one position, namely essentially perpendicular to the base body 1, and can be separated from it again. In all other positions the mounting on the mounting pin 16 allows only the rotation of the swivel arm 14 around the mounting pin 16.

To preserve the greatest possible range of rotation for the swivel arm 14 and the rotatable clamping jaw 5, the positioning points of the components 5 and 14 are positioned opposite one another on the plate 6.

Alternatively it is also possible, of course, to position the positioning points of components 5 and 14 on one side of the plate 6 and to configure the swivel arm 14, for instance, as divided in two parts spanning the entire clamping device 2.

For comfort in handling the device, on the ends opposite the positioning ends, both of the rotatable clamping jaw 5 and of the swivel arm 14 of the cutting device 3, hand grips 18 are formed permitting components 5 and 14 to be rotated easily. In addition, the illustrated device comprises a handle 18 formed on the plate 6 of the rigid clamping jaw 4 in order, first, to be able to offer sufficient clamping force by gripping the handgrips 18 of both clamping jaws 4 and 5 and, second, to be able to transport the ground body 1 with the rigid clamping jaw 4 easily and safely.

After installing the rotatable clamping jaw 5 and the swivel arm 14, the device is ready for use.

To install a tissue block for treatment in the clamping device 2, first the rotatable clamping jaw 5 and the swivel arm 14 of the cutting device 3 are rotated upward in the direction of the perpendicular position until they contact one another. Then a transplanted piece of cartilage or a different tissue piece, for instance, is inserted into the window-like opening 8 of the plate 6 and is clamped in by moving the rotatable clamping jaw 5 securely and immovably downward, so that the tooth-like fixing elements 13 ensure an additional support.

The actual free preparation of the tissue disc occurs in the next working step by moving downward the swivel arm 14. The two cutting edges 15 positioned on the parallel arm parts 17 simultaneously execute two parallel cuts with the downward motion of the swivel arm 14 and thus produce the required tissue disc in just one working step.

The width of the tissue disc that is to be prepared can be achieved either by altering the width of the intermediate space 7 formed between the side walls of the double-walled plate 6 or by altering the distance between the two arm parts 17 of the swivel arm 14 of the cutting device 3. These distances can be altered, for instance, either by a thread, where the alteration of these distances can be provided with a scale and can be adjusted by means of the handgrip 18 or one or more additional handgrips, adjusting screws, rotary knobs, or the like.

Here it is possible, first, merely to adjust the distance of the two cutting edges 15 to one another or, second, in addition to adjust the intermediate space 7 between the side walls of the double-walled plate 6, that is, the distance of the two side walls of the double-walled plate 6 to one another.

In addition to its simplicity of structure, a device constructed in this manner for preparing tissue discs is distinguished by its safe and precise handling.

What is claimed is:

1. A device for preparing tissue discs, having a clamping device for securing a tissue block by clamping and having at least one cutting device for treating the tissue block held in the clamping device, said clamping device comprising one rigid clamping jaw mounted on a base body and one rotatable clamping jaw that can rotate with respect to the rigid clamping jaw, wherein the rigid clamping jaw is configured as a double-walled plate and the rotatable jaw member being positioned in an intermediate space formed by the double-walled plate, and wherein the cutting device includes a swivel arm that is mounted on the plate of the rigid clamping jaw so as to be displaceable with respect to the clamping device and said cutting device being equipped with at least one cutting edge and wherein the swivel arm, at least in the area of the at least one cutting edge, comprises two arm parts running parallel to one another, each equipped with a cutting edge, which arm parts are mounted on the plate of the rigid clamping jaw in such a way that the plate is positioned between the two arm parts and between the cutting edges of the two arm parts.

2. The device according to claim 1, wherein, with the clamping device in closed position, a clamping gap remains between the at least two clamping jaws ridge clamping jaw and the rotatable clamping jaw of the clamping device.

3. The device according to claim 2, wherein the height of the clamping gap is adjustable.

4. The device according to claim 1, wherein the double-walled plate of the rigid clamping jaw comprises an opening for inserting the tissue block and the clamping jaw that can rotate with respect to the rigid clamping jaw is mounted so that the rotatable clamping jaw can move between the two side walls of the double-walled plate that are at a distance from one another.

5. The device according to claim 4, wherein the rotatable clamping jaw is mounted with one side in the plate of the rigid clamping jaw.

6. The device according to claim 3, wherein the height of the clamping gap can be adjusted by displacing the mounting point of the rotatable clamping jaw in the plate.

7. The device according to claim 1, wherein fixing elements formed as teeth are configured at least on the surfaces of the at least two clamping jaws rigid clamping jaw and the rotatable clamping jaw that face one another.

8. The device according to claim 1, wherein the swivel arm is mounted so that the swivel arm can rotate on the plate of the rigid clamping jaw.

* * * * *